United States Patent [19]  [11] 4,096,343
Yankee  [45] Jun. 20, 1978

[54] 8β,12α-PGF$_{2β}$15-ETHERS

[75] Inventor: Ernest W. Yankee, Portage, Mich.

[73] Assignee: The Upjohn Company, Kalamazoo, Mich.

[21] Appl. No.: 660,301

[22] Filed: Feb. 23, 1976

Related U.S. Application Data

[60] Continuation of Ser. No. 518,694, Oct. 19, 1974, abandoned, which is a division of Ser. No. 374,405, Jun. 28, 1973, which is a continuation-in-part of Ser. No. 289,317, Sep. 15, 1972, abandoned.

[51] Int. Cl.$^2$ ............................................ C07C 177/00
[52] U.S. Cl. ................................ 560/121; 260/514 D; 560/231
[58] Field of Search ........................ 260/468 D, 514 D

[56] References Cited

U.S. PATENT DOCUMENTS 3,862,984   1/1975   Pike et al. ............................ 260/514

*Primary Examiner*—Robert Gerstl
*Attorney, Agent, or Firm*—Robert A. Armitage

[57] ABSTRACT

This invention is a group of 8-beta, 12-alpha-PG$_2$ (prostagiandin-type) analogs having variable chain length, or methyl or phenyl substitution in the hydroxy-substituted side-chain, and processes for making them. These compounds are useful for a variety of pharmacological purposes, including anti-ulcer, inhibition of platelet aggregation, increase of nasal patency, and labor inducement at term.

1 Claim, No Drawings

$8\beta,12\alpha$-PGF$_{2\beta}$15-ETHERS

CROSS REFERENCE TO RELATED APPLICATIONS

The present application is a continuation application of Ser. No. 518,694, filed Oct. 29, 1974, now abandoned; which is a divisional application of Ser. No. 374,405, filed June 28, 1973, now pending issuance as a United States Patent; which is a continuation-in-part of Ser. No. 289,317, filed Sept. 15, 1972, now abandoned.

The present invention relates to prostaglandin analogs, for which the essential material constituting disclosure therefor is incorporated by reference here from U.S. Ser. No. 518,436, filed Oct. 29, 1974, issued as U.S. Pat. No. 3,969,396 on July 13, 1976; which application is a divisional application of Ser. No. 374,405.

I claim:

1. An optically active compound of the formula

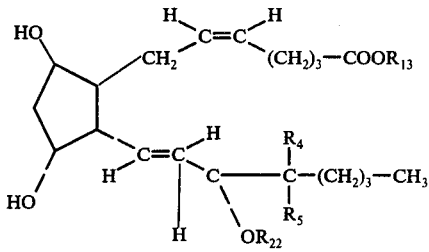

wherein $R_4$, $R_5$, and $R_7$ are hydrogen or methyl, being the same or different;

wherein $R_{13}$ is hydrogen, alkyl of one to 10 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive;

wherein $R_{22}$ is alkyl of one to 4 carbon atoms, inclusive;

including the lower alkanoates thereof, and the pharmacologically acceptable salts thereof wherein $R_{13}$ is hydrogen.

* * * * *

UNITED STATES PATENT OFFICE
CERTIFICATE OF CORRECTION

Patent No. 4,096,343　　　　　　　　Dated　　June 20, 1978

Inventor(s)　　Ernest W. Yankee

It is certified that error appears in the above-identified patent and that said Letters Patent are hereby corrected as shown below:

[60] should read -- Continuation of Ser. No. 518,694, Oct. 29, 1974, --

Column 2, lines 7-11, That portion of the formula should read

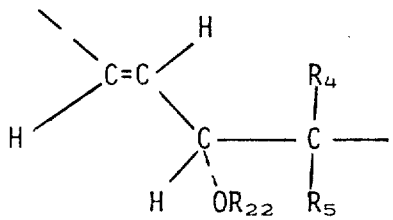

instead of as shown in the patent.

Signed and Sealed this

Sixteenth Day of January 1979

[SEAL]

Attest:

RUTH C. MASON
*Attesting Officer*

DONALD W. BANNER
*Commissioner of Patents and Trademarks*